Figure 1:
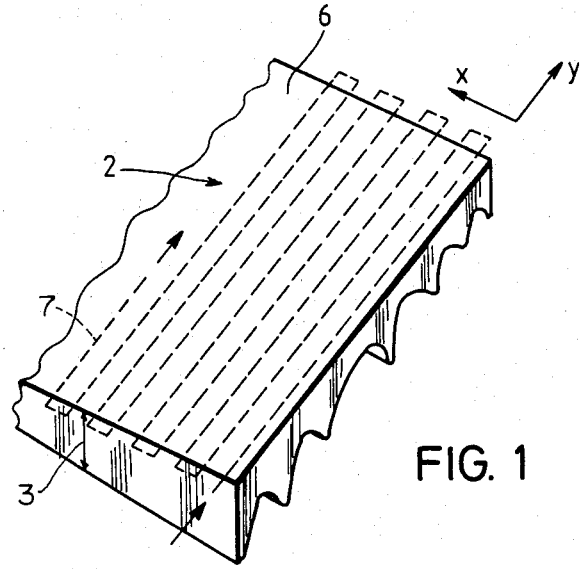

United States Patent [19]

Zimmermann et al.

[11] Patent Number: 4,489,611

[45] Date of Patent: Dec. 25, 1984

[54] MATERIAL TESTING APPARATUS USING ULTRASONIC TESTING HEADS

[75] Inventors: Werner Zimmermann; Helmar Langer, both of Munich, Fed. Rep. of Germany

[73] Assignee: Messerschmitt-Boelkow-Blohm Gesellschaft mit beschraenkter Haftung, Munich, Fed. Rep. of Germany

[21] Appl. No.: 459,391

[22] Filed: Jan. 20, 1983

[30] Foreign Application Priority Data

Feb. 5, 1982 [DE] Fed. Rep. of Germany ....... 3203862

[51] Int. Cl.³ ............................................. G01N 29/04
[52] U.S. Cl. ........................................ 73/625; 73/641
[58] Field of Search .................. 73/625, 624, 628, 641, 73/626, 618, 633, 634

[56] References Cited

U.S. PATENT DOCUMENTS

| | | | |
|---|---|---|---|
| 3,147,613 | 9/1964 | Kirkhope | 73/625 X |
| 3,978,714 | 9/1976 | Shraiber | 73/625 |
| 4,052,888 | 10/1977 | Brown | 73/625 |
| 4,143,553 | 4/1979 | Martens | 73/625 |
| 4,305,297 | 12/1981 | Ries | 73/628 |

Primary Examiner—Stephen A. Kreitman
Assistant Examiner—Vincent P. Kovalick
Attorney, Agent, or Firm—W. G. Fasse; D. H. Kane, Jr.

[57] ABSTRACT

Materials and structural components having irregular shapes may be tested by two ultrasonic testing heads which are movable in unison in the direction in which the cross-section of the material or component being tested changes. The synchronously moving testing heads are spaced from each other in a direction extending across the moving direction. The testing heads are ultrasonic receivers connected with their outputs to a comparing device which provides an error signal when the amplitude ratio of the received signal changes. The amplitude ratio is formed between the amplitudes of the ultrasonic signals received by both testing heads. Preferably, the comparing device comprises an amplifier which amplifies the amplitude of the received second signal by an amplification factor which is proportional to a deviation of the amplitude of the received first signal from a reference value. The error signal is recorded, for example, by a coordinate plotter.

5 Claims, 3 Drawing Figures

MATERIAL TESTING APPARATUS USING ULTRASONIC TESTING HEADS

CLAIM TO PRIORITY

The present invention is based on German Ser. No. P32 03 862.3, filed in the Federal Republic of Germany on Feb. 5, 1982. The priority of the German filing date is claimed for the present application.

BACKGROUND OF THE INVENTION

The present invention relates to a material testing apparatus using ultrasonic testing heads. Such apparatus is useful for testing materials and structural components having non-uniform cross-sections, by employing ultrasonic sound waves. The two testing heads are movable in unison in the direction of changes in the cross-section of an item to be tested. However, it is conceivable that the relative movement between the testing heads and the item to be tested may also be accomplished by keeping the testing heads stationary and moving the material to be tested past the testing heads.

Prior art testing devices of this type are limited to testing of materials and structural components having a constant cross-section or wall thickness. Such prior art devices are available in several versions. One version comprises a single ultrasonic transmitter and ultrasonic receiver. Another version comprises several transmitter and receiver units operating independently of one another for the purpose of covering a larger scanning width. Such transmitter and receiver units are guided simultaneously over the surface of an item to be tested. In any event, these prior art systems are, as mentioned, limited to items having a constant wall thickness. Stated differently these prior art devices are not suitable for a volumetric testing of structural components having an irregular cross-sectional geometry because the output signals provided by such prior art systems do not make it possible to ascertain whether a change in the amplitude of the received signal is due to a fault in the material or due to a change in the geometry of the structural component. Such distinguishing becomes possible in the prior art only with the aid of rather involved and time consuming procedures which, for example, involve measuring the structural component either prior or after the testing, whereby with the aid of the measurements the instantaneous thickness of the structural component and its geometry along its entire length to be tested is taken into account to establish a fault limit curve. The instantaneous value of the ultrasonic amplitude passing therough the item to be tested is then compared with such fault limit curve during the interpretation of the test results.

OBJECTS OF THE INVENTION

In view of the above it is the aim of the invention to achieve the following objects singly or in combination:

to provide an ultrasonic testing system which makes it possible to distinguish between signal changes due to true fault and a signal change due to a variation in the structural geomertry of an item being tested;

to provide an ultrasonic testing system which produces automatically and independently of any changes in the material or structural thickness and geometry a fault indication, thereby avoiding a preceding or subsequent ascertaining of a fault limit value curve which takes cross-sectional changes of the structural component into account;

to evaluate a relative value between two received testing signal amplitudes rather than the absolute value of such amplitudes, more specifically, to employ an amplitude difference as a fault indication; and to provide a testing system employing ultrasonic energy which is applicable even for testing materials and structural components which are hardly accessible or which have such a complicated geometry that the testing can be performed only from a surface of the structural component.

SUMMARY OF THE INVENTION

According to the invention this testing system comprises two ultrasonic testing receiver heads operating in synchronism and held spaced from one another in a direction extending substantially perpendicularly to the direction of relative movement between the testing apparatus and the item being tested. The outputs of the receiver heads are connected to a comparing stage which produces a fault signal in response to a change of the ratio of the received signal amplitude of one testing head relative to the received signal amplitude of the other testing head.

The influence of the thickness of an item being tested and of its geometry is automatically eliminated according to the invention in the testing head arrangement by not evaluating the absolute values of the received signal amplitude of a single testing head, but rather by evaluating the relative value between the received signal amplitudes of two ultrasonic testing receiver heads which are closly spaced from each other for ascertaining faults in the material or structural component. Due to the special signal combination according to the invention the output signal of the testing system remains uninfluenced by irregular changes in the cross-section of the structural component which changes extend in the direction of relative movement. Additionally, in the absence of a fault the output signal remains constant even if the thickness or geometry of the structural component has linear changes in a direction perpendicularly to the displacement direction. However, as soon as a fault travels into the path of the ultrasonic beam of one of the two receiver testing heads, the ratio between the received signal amplitudes changes, whereby the comparing stage produces a fault signal. Thus, it becomes possible according to the invention to recognize fault locations in a very simple manner even in structural components having a complicated geometry. Such ascertaining is accomplished with a high reliability without the need for a complicated, time consuming comparing of the measured results with a separately established fault limit or rated value curve for a reference structural component having the same geometry as the component being tested. Such reference structural component would have to be free of faults which may be difficult to achieve depending on the type of structural component involved.

The invention ascertains the change of the amplitude ratio with a circuit arrangement of simple construction, yet providing a high precision. For this purpose the present circuit arrangement comprises at least one comparing stage, including an amplifier which amplifies the second signal amplitude by a variable amplification factor which is proportional to the deviation of the first signal amplitude from a constant reference value. The output of the amplifier is connected to a comparator which ascertains the difference between the amplified second received signal amplitude and the reference value. The output of the comparator is connected to a detector which produces a fault signal when the difference changes. Due to the special preamplification of the received signal amplitudes the invention employs an amplitude difference as an indication of the presence of a fault. Such amplitude difference remains at a constant value until one of the two receiver testing heads travels over a fault location. At that moment the mentioned difference between the two received amplitudes either increases or decreases significantly. In those instances where the item to be tested changes its cross-sectional configuration exclusively in the displacement direction, or rather in the relative movement direction, the difference signal remains at zero until one of the two receiver testing heads travels over a fault location.

The present invention may be employed in connection with the so-called single passage sonic irradiation method whereby the transmitter head and the corresponding receiver head are arranged on opposite sides of the structural component. However, the invention is equally suitable for use in connection with the so-called double passage sonic irradiation method. In both instances it is possible to provide a single transmitter head for cooperation with two receiver testing heads. In connection with the double passage sonic irradiation method it is possible that one or the other head may be constructed to work also as a sonic transmitter. However, having regard to a high reliability it is suggested that each receiver testing head cooperates with its own transmitter testing head arranged at a fixed spacing from each other in the relative movement direction. The two transmitter heads operate in synchronism. If it is desired to provide for a double passage sonic irradiation, the transmitter head and the respective receiver head forming a pair are arranged at an angular slant relative to one other in order to provide the advantage that the receiver and transmitter heads may be arranged on one side of a structural component. This feature is especially applicable to testing structural components which are not easily accessible or which have a complicated shape or geometry, because in this type of arrangement the testing may be accomplished from one surface of the item to be tested.

BRIEF FIGURE DESCRIPTION

Figure 2:
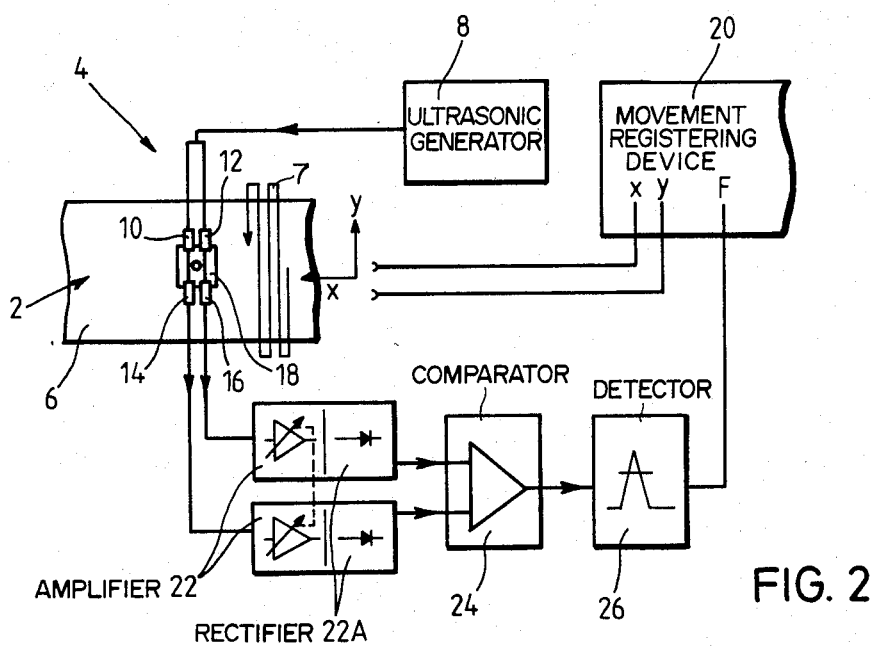
Figure 3:
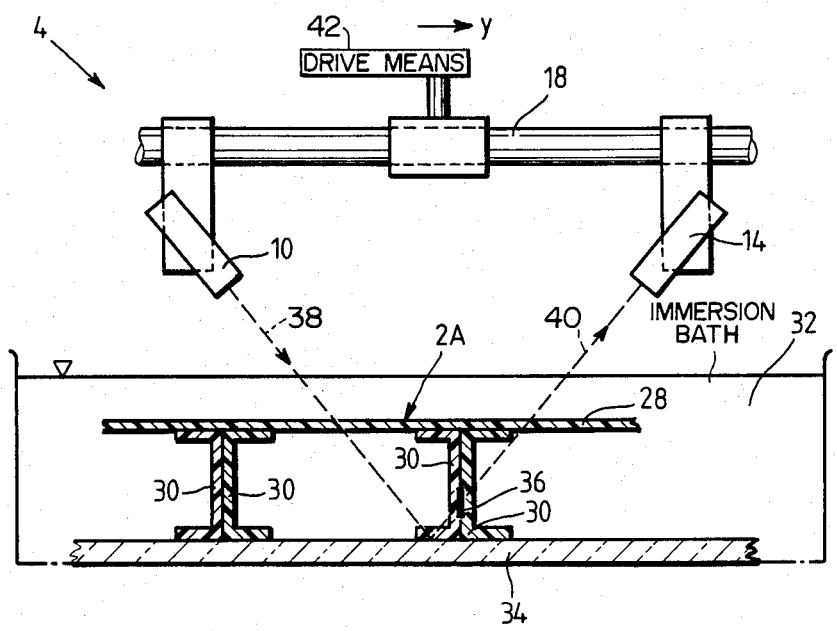

In order that the invention may be clearly understood, it will now be described, by way of example, with reference to the accompanying drawings, wherein:

FIG. 1 is a simplified, perspective partial view of an item to be tested by an apparatus according to the invention, said item having a solid structure and a non-uniform cross-section;

FIG. 2 is a block circuit diagram of a testing apparatus according to the invention; and FIG. 3 is a side view of a transmitter and receiver testing head pair arranged for a double passage sonic irradiation of an item to be tested, whereby the item has an open cross-sectional configuration including reinforcing or stiffening bars extending in a direction perpendicularly to the relative displacement movement of the testing head arrangement.

DETAILED DESCRIPTION OF PREFERRED EXAMPLE EMBODIMENTS AND OF THE BEST MODE OF THE INVENTION

FIG. 1 illustrates a panel type structural component which is to be tested. The structural component has an irregular cross-sectional shape which changes in the y-direction. Perpendicularly to the y-direction, that is in the x-directon, the structural component 2 has a diminishing thickness 3. The reduction of the wall thickness of the structural component 2 in the x-direction is linear. A testing sample such as shown in FIG. 1 is tested with an apparatus as shown in FIG. 2. For this purpose the testing head arrangement 4 is moved relative to the testing item 2 in the y-direction as indicated by the dashed lines 7 shown in FIG. 1. The testing arrangement 4 is moved along the surface 6 of the structural component 2 and at each end of the structural component a relative displacement in the x-direction takes place as indicated by the meandering shape of the dashed line 7 in FIG. 1. The relative displacement may be accomplished by moving either the testing device 4 or the work piece 2 being tested. The mechanical means for such relative movement are well known in the art and not part of the invention.

FIG. 2 shows a testing device 4 according to the invention comprising two ultrasonic transmitter heads 10 and 12 operatively connected to an ultrasonic generator 8. The transmitter heads 10 and 12 operate in synchronism with each other. The transmitter heads 10 and 12 are secured to a carrier 18 which is movable back and forth in the y-direction as indicated by the meandering line 7. This movement may be accomplished by conventional drive means 42 shown in FIG. 3. The carrier 18 also supports two testing ultrasonic receiver heads 14 and 16 held in a fixed position relative to the respective transmitter heads 10 and 12. The receiver heads 14 and 16 also work in synchronism with each other. Further, in the y-direction the spacing between the transmitter head 10 and the receiver head 14 and the spacing between the transmitter head 12 and the receiver head 16 are constant. In the x-direction which extends perpendicularly to the movement or y-direction testing heads 10 and 14, forming a pair, are closely spaced from the second pair of testing heads 12 and 16. The movements of the support 18 in the x- and y-directions are recorded by a movement registering device 20, such as a coordinate plotter.

In operation, the ultrasonic testing of a structural component 2 may take place, for example, in accordance with the double passage sonic irradiation method. In that method the ultrasonic waves travel from the transmitter heads 10 and 12 to the surface of the structural component 2 facing the testing apparatus and then through the structural component to the lower surface thereof where the ultrasonic energy is reflected to pass again through the structural component 2 to be received by the receiver heads 14 and 16 which convert the received energy into measured signals having respective amplitudes. The travel of the ultrasonic energy is shown by the dashed line paths 38 and 40 in FIG. 3.

Referring further to FIG. 2 each testing head output of the testing heads 14 and 16 is connected to its respective amplifier 22. At least one of the amplifiers provides a signal amplification by a variable amplification factor which is proportional to the deviation of the respective received amplitude from a constant reference value which may be adjusted by the respective bias of the amplifier. Thus, the respective amplitude is amplified to a predetermined constant value. Simultaneously, the output amplitude of the second receiver head 16 is amplified by the same amplification factor. The outputs of the amplifiers 22 are connected to respective rectifier circuits 22A which in turn supply the rectified measured signal to the two inputs of a comparator 24 which forms the difference between the amplified measured signals representing the amplitudes of the ultrasonic waves which travelled twice through the test sample 2.

Due to the illustrated displacement direction and due to the described relative arrangement of the testing heads to each other and to the test sample 2, the influence of any changes in the cross-section of the sample 2 is proportionally effective on both signal amplitudes. As a result, the difference ascertained by the comparator 24 remains constant until a fault location in the structural component travels into the beam path 38, 40 of one or the other testing head pairs 10 and 14 or 12 and 16. Thus, a detector 26 connected to the output of the comparator 24 monitors this difference between the two amplified received signal amplitudes and produces a fault representing signal F as soon as this differnce deviates from the mentioned constant value. The fault representing signal F is supplied by the detector 26 to a recoding input of the movement registering device 20 and may be displayed, for example, on a graph which also displays the respective x and y coordinates.

FIG. 3 illustrates the arrangement of the testing device 4 with its support 18 arranged above a test sample 2A in a ultrasonic wave conducting bath 32. The pair of testing heads 10 and 14 is seen in FIG. 3. However, the second pair of testing heads 12 and 16 is to be visualized as located directly behind the heads 10 and 14 and at the same elevation as the heads 10 and 14. The transmitter head 10 and the receiver 14 are arranged at an angle relative to the test sample 2A so that the ultrasonic energy may travel along the angular path 38 and 40 relative to the horizontal thereby passing twice through the test sample 2A, once before and once after reflection by a glass plate 34. The structural component or test sample 2A is a fiber compound structure having an open cross-section, for example, as used in the wing of an aircraft structure. The test sample 2A comprises a planking layer 28 and reinforcing or stiffening bars 30 having a U-shaped cross-section and glued to each other as shown to provide a localized reinforcement of the planking 28 having a constant wall thickness. In order to assure an accurate testing of the entire volume of the structural component 2A to ascertain fault locations such as shrinkage or cavities in the planking 28 or in the bars 30 or delaminating locations in the adhesive interfaces, the structural component 2A is immersed in an immersion bath 32 having good sound conducting qualities. The structural component 2A is resting on a sonic reflector such as a glass plate 34, whereby the ultrasonic energy travels twice through the test sample as mentioned above when the support or carriage 18 is driven by conventional drive means 42 in the y-direction and displaced at each end of its y-direction travel by a short distance in the x-direction to achieve the above mentioned meandering pattern. In the described arrangement changes in the thickness of the structural component and in its geometry are again eliminated due to the arrangement of the testing heads whereby difference ascertained by the comparator 24 from the two received amplitudes which have been amplified by the variable amplification factor, remains constant as long as no fault location is present in the structural component. If the ultrasonic wave-forms 38, 40 travel through a fault such as a delamination location 36 between the bars 30 a significant change is noticed in the difference formed by the comparator and such changes are detected by the detector 26 which generates the fault signal F as mentioned above.

Due to the above arrangement shown in FIG. 3, each fault location 36 is indicated twice by the registering device 20. Once the indication takes place when the fault location 36 is coming into the reflected beam 40, as shown at 36 in FIG. 3. The second time the fault location is indicated again when it comes into the incoming beam path 38 after the support 18 has been displaced by a predetermined distance in the y-direction. As a result, the registering device 20 registers not only the location of the fault but also its projected profile. Thus, two identical fault location displays appear in the registering device 20 for the same x-location. Such display is evaluated as a single fault due to the double passage of the ultrasonic beam. The geometric mean value of the y-coordinates of these two identical fault displays provides the actual y-coordinate of the fault location.

Although the invention has been described with reference to specific example embodiments, it will be appreciated, that it is intended, to cover all modifications and equivalents within the scope of the appended claims.

What is claimed is:

1. A testing apparatus for testing materials and structural components having irregular cross-sections, comprising testing means including first and second ultrasonic testing receiver heads (14, 16) operating in synchronism, first and second ultrasonic transmitter heads (10, 12) also operating in synchronism with each other for transmitting ultrasonic wave energy to be received by said first and second ultrasonic testing receiver heads, and means (18) for operatively supporting said first and second ultrasonic testing receiver heads and said first and second ultrasonic transmitter heads in a fixed position relative to each other and relative to an item to be tested, said apparatus further comprising means operatively arranged for allowing relative movement in a defined direction (y) between said testing means and an item to be tested, said first and second ultrasonic testing receiver heads (14, 16) being spaced from each other on said supporting means (18) in a direction (x) extending substantially perpendicularly to said defined direction (y) of relative movement, said first and second ultrasonic transmitter heads (10, 12) being spaced from their respective ultrasonic receiver head (14, 16) in the defined direction (y) of relative movement, and comparing means (22, 24, 26) operatively connected to said testing receiver heads (14, 16) for comparing an output signal amplitude from said first testing receiver head with an output signal amplitude from said second testing receiver head and for producing a fault signal in response to a change in the amplitude ratio between the received signal amplitudes.

2. The apparatus of claim 1, wherein said comparing means comprise amplifier means (22) operatively connected to said second testing receiver head for amplifying said output signal amplitude from said second testing receiver head by an amplification factor which is proportional to a deviation of said output signal amplitude of said first testing receiver head from a constant reference value, said comparing means further comprising a comparator operatively connected to said amplifier means which ascertains the difference between the amplified amplitude of the output signal of the second testing receiver head and said constant value, and detector means connected to said comparator for producing said fault signal in response to a variation in said difference.

3. The apparatus of claim 1, wherein each one of said testing receiver heads and each one of said transmitter heads form a pair so that two pairs are provided, and wherein the heads of a pair are arranged in such a position with an angular slant relative to each other that ultrasonic wave energy passes twice through an item to be tested.

4. The apparatus of claim 1, wherein said comparing means comprise two amplifiers (22) each connected with its input to its respective testing receiver head for amplifying the respective output signal amplitude, each amplifier having adjustment means for providing an amplification factor which is variable in accordance with the deviation of one of the output signal amplitudes from a constant reference value whereby each output signal amplitude of said two testing receiver heads is amplified in accordance with a variable amplification factor which is proportional to said deviation, a comparator (24) having two inputs each operatively connected to its respective one of said amplifiers for producing a difference signal representing the difference between the amplifier output signals, and detector means (26) operatively connected to said comparator (24) for producing a fault signal in response to a variation in said difference signal.

5. A testing apparatus for testing materials and structural components having irregular cross-sections, comprising testing means including first and second ultrasonic testing receiver heads (14, 16) operating in synchronism, first and second ultrasonic transmitter heads (10, 12) also operating in synchronism with each other for transmitting ultrasonic wave energy to be received by said first and second ultrasonic testing receiver heads, and means (18) for operatively supporting said first and second ultrasonic testing receiver heads and said first and second ultrasonic transmitter heads in a fixed position relative to each other and relative to an item to be tested, said apparatus further comprising means operatively arranged for allowing relative movement in a defined direction (y) between said testing means and an item to be tested, said first and second ultrasonic testing receiver heads (14, 16) being spaced from each other on said supporting means (18) in a direction (x) extending substantially perpendicularly to said defined direction (y) of relative movement, said first and second ultrasonic transmitter heads (10, 12) being spaced from their respective ultrasonic receiver head (14, 16) in the defined direction (y) of relative movement, and comparing means (22, 24, 26) operatively connected to said testing receiver heads (14, 16) for comparing an output signal amplitude from said first testing receiver head with an output signal amplitude from said second testing receiver head and for producing a fault signal in response to a change in the amplitude ratio between the received signal amplitudes, wherein said comparing means comprise two amplifiers (22) each connected with its input to its respective testing receiver head for amplifying the respective output signal amplitude, one of said amplifiers amplifying the amplitude of a signal received from its respective receiver head to a predetermined constant reference value, the other of said amplifiers amplifying the amplitude of a signal received from its respective receiver head in accordance with an amplification factor which is proportional to an amplification value of said one amplifier, said comparing means further comprising a comparator connected for producing a difference signal between said constant reference value and the signal amplitude amplified by said other amplifier, and a detector connected to said comparator for producing said fault signal when there is a change in said difference signal.

* * * * *